United States Patent
Lee et al.

(10) Patent No.: US 10,717,991 B2
(45) Date of Patent: Jul. 21, 2020

(54) TRANSGENIC PIG WHICH SIMULTANEOUSLY EXPRESSES HO-1 GENE AND TNFR1-FC GENE, AND COMPRISES KNOCKED-OUT GGTA1 GENE, AND USE THEREOF

(71) Applicants: SEOUL NATIONAL UNIVERSITY R&DB FOUNDATION, Seoul (KR); CHONG KUN DANG PHARMACEUTICAL CORP., Seoul (KR)

(72) Inventors: Byeong Chun Lee, Seoul (KR); Curie Ahn, Seoul (KR); Geon A Kim, Seoul (KR); Su Cheong Yeom, Gangwon-do (KR); Su Jin Kim, Seoul (KR); Bumrae Cho, Seoul (KR); Eun Mi Lee, Seoul (KR); Sang Hoon Lee, Seoul (KR); In Chang Hwang, Gyeonggi-do (KR); Hye Jin Hong, Gyeonggi-do (KR)

(73) Assignees: CHONG KUN DANG PHARMACEUTICAL CORP., Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 78 days.

(21) Appl. No.: 15/775,751

(22) PCT Filed: Nov. 11, 2016

(86) PCT No.: PCT/KR2016/012993
§ 371 (c)(1),
(2) Date: Oct. 9, 2018

(87) PCT Pub. No.: WO2017/082667
PCT Pub. Date: May 18, 2017

(65) Prior Publication Data
US 2019/0024115 A1 Jan. 24, 2019

(30) Foreign Application Priority Data
Nov. 13, 2015 (KR) .......... 10-2015-0159976

(51) Int. Cl.
| | | |
|---|---|---|
| A01K 67/00 | (2006.01) |
| C12N 15/85 | (2006.01) |
| A01K 67/027 | (2006.01) |
| C12N 9/02 | (2006.01) |
| C12N 9/10 | (2006.01) |
| C07K 14/705 | (2006.01) |
| C12N 15/877 | (2010.01) |
| C12N 15/52 | (2006.01) |
| C12N 15/62 | (2006.01) |

(52) U.S. Cl.
CPC ........ *C12N 15/8509* (2013.01); *A01K 67/027* (2013.01); *A01K 67/0271* (2013.01); *A01K 67/0276* (2013.01); *A01K 67/0278* (2013.01); *C07K 14/70575* (2013.01); *C07K 14/70578* (2013.01); *C12N 9/0071* (2013.01); *C12N 9/1051* (2013.01); *C12N 15/52* (2013.01); *C12N 15/62* (2013.01); *C12N 15/8778* (2013.01); *C12Y 114/14001* (2013.01); *C12Y 204/01087* (2013.01); *A01K 2217/052* (2013.01); *A01K 2217/072* (2013.01); *A01K 2217/075* (2013.01); *A01K 2217/15* (2013.01); *A01K 2217/206* (2013.01); *A01K 2227/108* (2013.01); *A01K 2267/025* (2013.01); *C07K 2319/30* (2013.01); *C12Y 114/99003* (2013.01)

(58) Field of Classification Search
CPC .................. A01K 67/027; C12N 15/8509
See application file for complete search history.

(56) References Cited

U.S. PATENT DOCUMENTS 9,018,439 B2 * 4/2015 Ahn .................... A01K 67/0275
800/17
2012/0278910 A1 11/2012 Ahn et al.

FOREIGN PATENT DOCUMENTS

| KR | 1020070113754 | 11/2007 |
| KR | 1020090053635 | 5/2009 |
| KR | 102011079485 | 7/2011 |
| KR | 1020140052093 | 5/2014 |
| KR | 1020150008719 | 1/2015 |

OTHER PUBLICATIONS

Naito et al. J Reprod Fert 113:137-143, 1998 (Year: 1998).*
Raina et al. Gene 96-100, 2015 (Year: 2015).*
Dolatshad et al. Mammalian Genome 26:598-608, 2015 (Year: 2015).*
Ezzelarab and Cooper. International Journal of Surgery 23:301-305, 2015 (Year: 2015).*
Yao et al. (Scientific Reports 4:6926. DOI:10.1038/srep06926. Nov. 2014. pp. 1-8 (Year: 2014).*

(Continued)

Primary Examiner — Marcia S Noble
(74) Attorney, Agent, or Firm — Gavrilovich, Dodd & Lindsey LLP

(57) ABSTRACT

The present invention relates to a transgenic pig in which an immune rejection response is suppressed during xenotransplantation, wherein a gene coding for heme oxygenase-1 (HO-1) and a gene coding for tumor necrosis factor receptor 1-Fc (TNFR1-Fc) are simultaneously expressed and a gene coding for α-1,3-galactosyltransferase (GGTA1) is knocked out; and a method for producing the same.

11 Claims, 9 Drawing Sheets

Specification includes a Sequence Listing.

(56) References Cited

OTHER PUBLICATIONS

Hauschild et al., "Efficient generation of a biallelic knockout in pigs using zinc-finger nucleases", PNAS, Sep. 6, 2011, vol. 108, No. 36, pp. 12013-12017.

Kim et al., "Production of talen-mediated gene-modified pigs via somatic cell nuclear transfer", Oct. 27, 2015, vol. 22, No. Suppl 1, p. S1, 81, #923 Abstracts if the IPITA-IXA-CTS 2015 Joint Congress.

\* cited by examiner

TRANSGENIC PIG WHICH SIMULTANEOUSLY EXPRESSES HO-1 GENE AND TNFR1-FC GENE, AND COMPRISES KNOCKED-OUT GGTA1 GENE, AND USE THEREOF

CROSS REFERENCE TO RELATED APPLICATIONS

This application is a U.S. National Stage Application filed under 35 U.S.C. 371 and claims priority to International Application No. PCT/KR2016/012993, filed Nov. 11, 2016, which application claims priority to Korean Application No. 10-2015-0159976, filed Nov. 13, 2015, the disclosures of which are incorporated herein by reference in their entirety.

TECHNICAL FIELD

The present invention relates to a transgenic pig in which an immune rejection response is suppressed during xenotransplantation, wherein a gene coding for heme oxygenase-1 (HO-1) and a gene coding for tumor necrosis factor receptor 1-Fc (TNFR1-Fc) fusion protein are simultaneously expressed and a gene coding for α-1,3-galactosyltransferase (GGTA1) is knocked out; and a method for producing the same.

BACKGROUND

Organ transplantation is the procedure of replacing diseased organs or parts of organs with healthy organs of another person when diseased organs lose their functions and drugs no longer help to treat the disease. However, many attempts have been made to address the problem of the lack of donors for transplantable organs. An example thereof includes stem cell xenotransplants, which is a therapeutic method of replacing damaged cells with stem cells that are differentiated and proliferated as much as needed. However, it has a limitation in that the stem cells cannot be developed into an organ consisting of different types of cells. Therefore, xenotransplantation may be considered for use in direct replacement of organs when needed.

One of the promising alternatives for human organs is xenotransplantation using animals capable of providing a sufficient quantity of donor organs, and attempts have been made to use many animals such as monkeys and pigs to supply organs for xenotransplantation. Among these, pigs have numerous similarities with humans in terms of anatomy and physiology, and their organs are similar in size than those of humans. In addition, pigs are easy to breed, and they have a short gestation period (112 days) and large litters (6 to 12 piglets). Owing to these advantages, the use of pigs' organs has been actively studied.

An immune rejection response is a serious problem for xenotransplantation using pigs, etc. Accordingly, the present inventors have succeeded in introducing a gene coding for human HO-1 and a gene coding for TNFR1-Fc fusion protein into pig cells, thereby producing a transgenic pig in which an immune rejection response is suppressed and cells are protected from oxidative stress, and in which an inflammatory response is suppressed (Korean Patent Publication No. 10-2011-0079485). However, the transgenic pig xenograft was not able to withstand hyper-acute rejection (HAR).

Technical Problem

The present inventors have made intensive efforts to develop a transgenic pig for organ transplantation, wherein, during xenotransplantation, the oxidative stress and inflammatory response are reduced and the hyper-acute rejection response is suppressed. As the results, they have completed the present invention by developing a transgenic pig in which a gene coding for human HO-1 and a gene coding for human TNFR1-Fc fusion protein are introduced and a gene coding for GGTA1 is knocked out.

Technical Solution

An objective of the present invention is to provide a transgenic pig in which an immune rejection response is suppressed during xenotransplantation, wherein a gene coding for human HO-1 and a gene coding for human TNFR1-Fc fusion protein are introduced and a gene coding for GGTA1 is knocked out; and a method for producing the same.

Another objective of the present invention is to provide a somatic donor cell line for producing the transgenic pig.

Still another objective of the present invention is to provide a method for producing a transplantable organ in which an immune rejection response is suppressed during xenotransplantation, comprising: producing the transgenic pig; and isolating a transplantable organ from the transgenic pig.

Advantageous Effects

The transgenic pig of the present invention, in which the genes coding for human HO-1 and TNFR1-Fc fusion protein are simultaneously expressed and the gene coding for GGTA1 is knocked out, may reduce oxidative stress during organ isolation and in vitro culture by antioxidative reaction, cytoprotective function, etc., and may also reduce a TNF-α-mediated inflammatory response in early transplantation by TNFR1-Fc expression. In addition, the transgenic pig may inhibit the maturation of dendritic cells and regulate the activation and proliferation of T-cells, thereby reducing an acute vascular rejection response to promote early engraftment of a transplanted organ. In addition, the transgenic pig can increase the viability of a transplanted organ by suppressing HAR reaction caused by GGTA1. Accordingly, an organ, in which an immune rejection response is suppressed during xenotransplantation, can be produced using the transgenic pig.

BEST MODE

Figure 1:
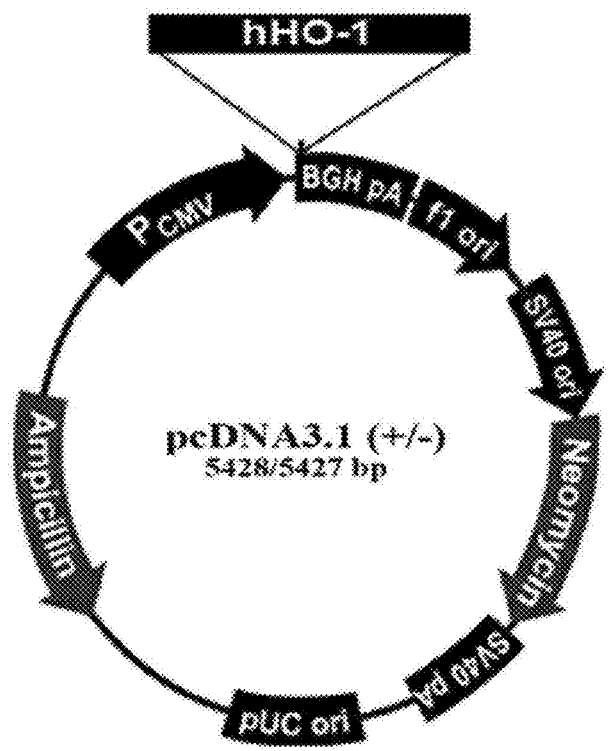
FIG. 1 is a schematic view of a cleavage map of an expression vector in which a gene coding for human HO-1 is inserted.

In one aspect to achieve the above objectives, the present invention provides a method for producing a transgenic pig in which an immune rejection response is suppressed during xenotransplantation, comprising: a) isolating somatic cells from a pig; b) introducing a gene coding for human HO-1 and a gene coding for human TNFR1-Fc fusion protein into the somatic cells, and knocking out a gene coding for GGTA1; c) selecting and culturing the somatic cells in which the gene coding for human HO-1 and the gene coding for human TNFR1-Fc fusion protein are introduced and the gene coding for GGTA1 is knocked out; and d) removing the nucleus from an oocyte of the pig and fusing it with the selected somatic cells to prepare an embryo transplanted with a somatic cell nucleus.

The present invention aims to produce a transgenic pig having such characteristics in order to produce organs, in which an immune rejection response is suppressed during xenotransplantation. Accordingly, in the present invention, a transgenic pig in which a gene coding for human HO-1 and a gene coding for human TNFR1-Fc fusion protein are expressed by introducing the same into the isolated somatic cells of a pig and in which a gene coding for GGTA1 is knocked out was prepared. Hereinafter, each step of the production method above will be described in detail.

As used herein, the term "transgenic pig" refers to a pig that is genetically modified by artificial insertion of a foreign piece of genes, which have been recombined, on the porcine chromosome or by knock-out of genes inherently possessed in the pig. The preferred animal is a pig, but the method of the present invention may be applied to mammals in nature capable of providing humans with their organs, so as to produce transgenic animals in which an immune rejection response is suppressed.

Step a) is a step of isolating somatic cells from a pig, which become a cell donor (or a nucleus donor) in production of a clone pig using nucleus substitution technology. Therefore, one of ordinary skill in the art can select and use a pig according to purposes, and the type of pig is not particularly limited. That is, the pig may be a fetal pig or an adult pig, and includes not only a natural pig but also a pig that is artificially transformed.

As used herein, the term "somatic cells" refers to cells which can be isolated from the pig, and the type thereof is not particularly limited as long as transduction is possible via gene insertion and gene knock-out, and may include both differentiated cells and undifferentiated cells.

As a method for isolating the somatic cells, any methods conventionally known in the art may be used without limitation.

Step b) is a step of transducing the isolated pig somatic cells. Specifically, it is a step of introducing a gene coding for human HO-1 and a gene coding for human TNFR1-Fc fusion protein into the somatic cells and knocking out a gene coding for GGTA1.

Step c) is a step of selecting the transduced cells and culturing the selected cells.

As used herein, the term "gene coding for HO-1" refers to a gene coding for an enzyme that is expressed in cells due to a variety of stresses such as heavy metals, endotoxin, ultraviolet, heat shock, reactive oxygen, hypoxia, and the like. HO-1 is an enzyme that ultimately degrades heme into bilirubin and $Fe^{2+}$, and is an antioxidant enzyme capable of cytoprotection via radical scavenging or apoptosis suppression and improving functions of the transplanted organ. In the present invention, HO-1 inhibits proliferation of CD4+ T-cells and activates proliferation of endothelial cells at the same time, thereby normalizing immune cells in the body. Consequently, immune rejection responses to xenotransplantation can be suppressed, and cells that make up the organ show resistance to oxidative stress when isolated and are protected via apoptosis suppression.

Specifically, the gene coding for human HO-1 can be obtained from a known gene database, and more specifically, it may include a nucleotide sequence of SEQ ID NO: 1. However, the gene may be included in the scope of the present invention without limitation as long as it can be introduced into somatic cells of pigs to express the function of HO-1.

As used herein, the term "gene coding for TNFR1-Fc fusion protein" refers to a gene coding for a fusion protein of the immunoglobulin Fc region and the extracellular domain of TNFR1, which is able to bind with TNF-α. As used herein, the terms "the gene coding for TNFR1-Fc fusion protein" and "the gene coding for TNFR1-Fc protein" are interchangeably used. In the present invention, any type of TNFR1-Fc protein may be used without limitation, as long as it is able to bind with TNF-α and inhibit TNF-α. In particular, a fusion protein of soluble tumor necrosis factor receptor 1 (soluble TNFR1, sTNFR1) and immunoglobulin Fc region may be used.

As used herein, the term "immunoglobulin Fc region" refers to the heavy-chain constant region 2 ($C_H2$) and the heavy-chain constant region 3 ($C_H3$) of an immunoglobulin, except for the variable regions of the heavy and light chains, the heavy-chain constant region 1 ($C_H1$) and the light-chain constant region 1 ($C_L1$) of the immunoglobulin. In addition, the immunoglobulin Fc region of the present invention may contain a part or all of the Fc region comprising the $C_H1$ and/or the $C_L1$, except for the variable regions of the heavy and light chains, as long as it has effects similar to or better than the native protein. In addition, the Ig Fc region may be a fragment having a deletion in a relatively long portion of the amino acid sequence of $C_H2$ and/or $C_H3$. That is, the immunoglobulin Fc region of the present invention may include 1) a $C_H1$ domain, a $C_H2$ domain, a $C_H3$ domain, and a $C_H4$ domain, 2) a $C_H1$ domain and a $C_H2$ domain, 3) a $C_H1$ domain and a $C_H3$ domain, 4) a $C_H2$ domain and a $C_H3$ domain, 5) a combination of one or more domains and an immunoglobulin hinge region (or a portion of the hinge region), and 6) a dimer of each domain of the heavy-chain constant regions and the light-chain constant region. The immunoglobulin Fc region of the present invention includes a native amino acid sequence, and a sequence derivative (mutant) thereof. An amino acid sequence derivative is a sequence that is different from the native amino acid sequence due to a deletion, an insertion, a non-conservative or conservative substitution, or combinations thereof of one or more amino acid residues. For example, in an IgG Fc, amino acid residues known to be important in binding, at positions 214 to 238, 297 to 299, 318 to 322, or 327 to 331, may be used as a suitable target for modification. Also, other various derivatives are possible, including one in which a region capable of forming a disulfide bond is deleted, or certain amino acid residues are eliminated at the N-terminus of a native Fc form or a methionine residue is added thereto. Further, to remove effector functions, a deletion may occur in a complement-binding site, such as a C1q-binding site and an ADCC site.

Techniques of preparing such sequence derivatives of the immunoglobulin Fc region are disclosed in International Patent Publication Nos. WO 97/34631 and WO 96/32478. Amino acid exchanges in proteins and peptides, which do not generally alter the activity of molecules, are known in the art. The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly in both directions. The Fc region, if desired, may be modified by phosphorylation, sulfation, acrylation, glycosylation, methylation, farnesylation, acetylation, amidation, and the like. The aforementioned Fc derivatives are derivatives that have a biological activity identical to the Fc region of the present invention or improved structural stability, for example, against heat, pH, or the like.

On the other hand, the immunoglobulin Fc region may be derived from humans or other animals including cows, goats, pigs, mice, rabbits, hamsters, rats, and guinea pigs, and preferably humans. In addition, the immunoglobulin Fc region may be an Fc region that is derived from IgG, IgA, IgD, IgE, and IgM, or that is made by combinations thereof or hybrids thereof. Preferably, it is derived from IgG or IgM, which are among the most abundant proteins in human blood, and most preferably from IgG, which is known to enhance the half-lives of ligand-binding proteins.

Meanwhile, the term "combination", as used herein, means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

The term "hybrid", as used herein, means that sequences encoding two or more immunoglobulin Fc regions of different origin are present in a single-chain immunoglobulin Fc region. In the present invention, various types of hybrids are possible. That is, domain hybrids may be composed of one to four domains selected from the group consisting of $C_H1$, $C_H2$, $C_H3$, and $C_H4$ of IgG Fc, IgM Fc, IgA Fc, IgE Fc, and IgD Fc, and may include the hinge region. On the other hand, IgG is divided into IgG1, IgG2, IgG3, and IgG4 subclasses, and the present invention includes combinations and hybrids thereof.

As used herein, the fusion protein of soluble cytokine receptor and immunoglobulin (hereinafter referred to as 'Ig') has the following advantages over a monomer of the intrinsic molecule or a molecule not fused to Ig:

1) the fusion protein has increased total avidity to a ligand because it has bivalency in a dimer form;

2) the fusion protein is present in an undestroyed form in serum for a longer period of time by virtue of increased molecular stability;

3) effector cells are activated by the Fc (fragment crystallizable) portion of the immunoglobulin heavy chain; and 4) the fusion protein is isolated and purified by a convenient method (e.g., isolation and purification using protein A).

The fusion protein of the present invention is manufactured in a form excluding the $C_H1$ domain of the heavy chain, resulting in a dimer form that does not bind with the light chain of immunoglobulin.

Specifically, the sequences of the genes coding for human TNFR1 and Fc may each be obtained from a known database. More specifically, the gene coding for TNFR1-Fc fusion protein represented by SEQ ID NO: 8 may be used, but any sequence may be used without limitation, as long as it is introduced into porcine somatic cells to show the functions of TNFR1-Fc fusion protein.

The gene introduction may be carried out using a known method capable of expressing the gene coding for human HO-1 and the gene coding for human TNFR1-Fc protein in porcine somatic cells, but is not limited thereto. For example, it may be carried out by introducing an expression vector including the genes, increasing the copy number of the corresponding gene in the genome, or by introducing or overexpressing the corresponding gene by substitution or modification of its promoter sequence.

The method of transducing the gene into cells may be performed by a biochemical method, a physical method, or a virus-mediated transfection method. Preferably, the biochemical method is performed using FuGene6 (Roche, USA), Lipofectamine (Lipofectamine™2000, Invitrogen, USA), or ExGen 500 (MBI Fermentas International Inc., Canada), and more preferably, lipid-mediated transfection using Lipofectamine. In addition, the expression vector comprising the gene may be any expression vector that can be expressed in porcine somatic cell lines. In the specific Example of the present invention, a pcDNA 3.1 vector was used as the expression vector comprising the gene coding for human HO-1, and a pcDNA6 vector was used as the expression vector comprising the gene coding for human TNFR1-Fc fusion protein.

Figure 2:
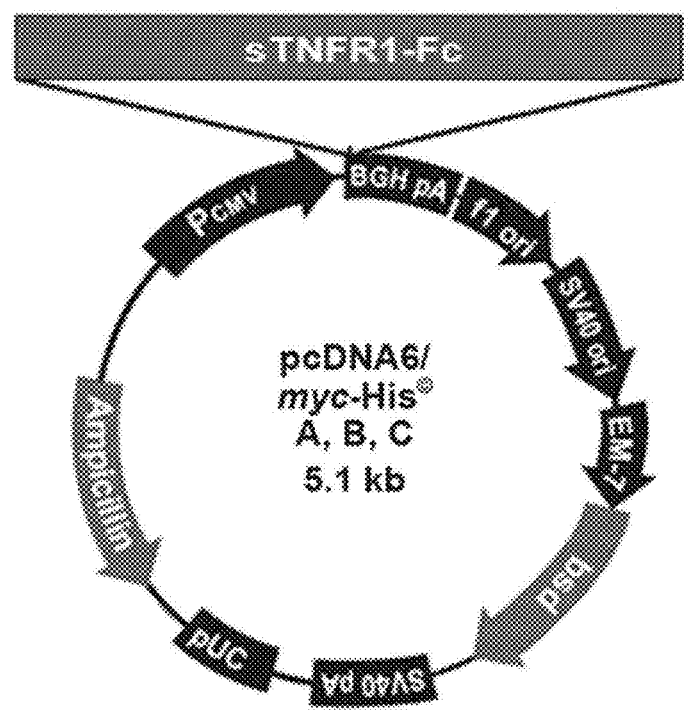
FIG. 2 is a schematic view of a cleavage map of an expression vector in which a gene coding for human sTNFR1-Fc fusion protein is inserted.
Figures 3, 4:
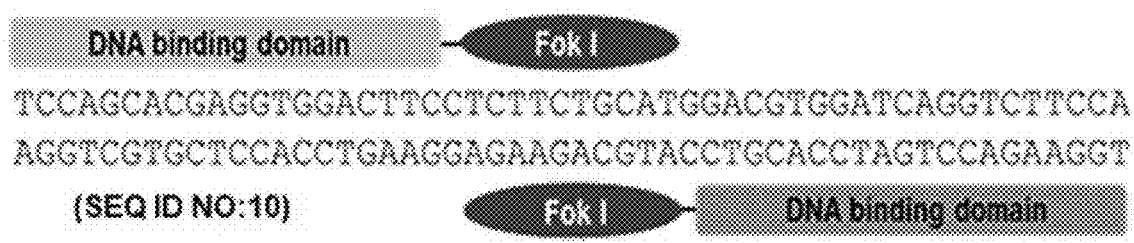
FIG. 3 is a schematic diagram of TALEN targeting the gene of the present invention, which encodes GGTA1.
FIG. 4 shows the result confirming through cloning and sequencing whether the genes of the cells selected after transduction of the gene coding for GGTA1 using TALEN were deleted.

In one preferred embodiment, step b) may be performed by introducing a single vector comprising the gene coding for human HO-1, particularly, a vector having a cleavage map of FIG. 1, and a single vector comprising the gene coding for human TNFR1-Fc fusion protein, particularly, a vector having a cleavage map of FIG. 4 into somatic cells, separately or simultaneously, but is not limited thereto. In one specific embodiment of the present invention, the gene coding for human HO-1 was inserted into the pcDNA3.1 vector, which is an expression vector comprising the neomycin resistance gene, so as to prepare the vector having the cleavage map of FIG. 1, and expression of the inserted gene was examined in an HEK239 cell line. In addition, the gene coding for human TNFR1-Fc fusion protein was inserted into the pcDNA6 vector, which is an expression vector comprising the blasticidin resistance gene, so as to prepare the vector having the cleavage map of FIG. 2, and expression of the inserted gene was examined in the HEK239 cell line.

As used herein, the term "vector" refers to an expression vector capable of expressing a target gene in cells introduced with the vector, and to a gene construct that includes essential regulatory elements to which a gene insert is operably linked in such a manner as to be expressed. For example, in the present invention, a recombinant vector comprising the gene coding for human HO-1 or the gene coding for human TNFR1-Fc fusion protein can be prepared, and the prepared recombinant vector is introduced into somatic cells, thereby preparing a donor cell line for the production of the transgenic embryos.

Specifically, the promoter used in the present invention may be any promoter commonly used in the art for the preparation of expression vectors, without limitation. Examples of the promoter to be used may include a CMV promoter, an SV40 promoter, and a CAG promoter, but the promoter sequences to be used in the present invention are not limited to these examples. If necessary, a particular promoter may be used for tissue-specific expression.

Additionally, the polyadenylation sequence of the present invention may be a commonly used polyadenylation sequence, for example, an SV40 polyadenylation sequence, a human growth hormone polyadenylation sequence, a mouse protamine-1 gene polyadenylation sequence (protamine-1 poly A signal), a large T antigen poly A region-derived polyadenylation sequence, rabbit β-globin-derived polyadenylation sequence, or fetal bovine growth hormone polyadenylation sequence, without limitation.

In order to examine expression of the gene coding for human HO-1 or the gene coding for human TNFR1-Fc fusion protein, the vector of the present invention may further include a tag sequence for isolation or purification of protein. Examples of the tag sequence may include GFP, GST (glutathione S-transferase)-tag, HA, His-tag, Myc-tag, and T7-tag, but the tag sequence of the present invention is not limited to these examples.

In a specific embodiment of the present invention, the HO-1 gene having the nucleotide sequence of SEQ ID NO: 1 was introduced into the pcDNA3.1 vector to produce a vector expressing the HO-1 gene (FIG. 1), and the sTNFR1-Fc gene having the nucleotide sequence of SEQ ID NO: 8 was introduced into the pcDNA6 vector to prepare a vector expressing the sTNFR1-Fc gene (FIG. 2). In another specific embodiment of the present invention, the two expression vectors were introduced into somatic cells isolated from pigs, and cells simultaneously expressing the HO-1 gene and sTNFR1-Fc gene were prepared. In addition, a transgenic pig was produced using the cells above.

As used herein, the term "gene coding for GGTA1" refers to a gene coding for an enzyme involved in the production of N-glycan in glycoprotein, wherein the enzyme binds galactose residues to galactose in the N-glycan through α-1,3 glycosidic bonds to form a terminal Gal-α-1,3-Gal (i.e., α-Gal) moiety. In the case of xenotransplantation which transplants a pig's organ to other species, a hyper-acute immune rejection response caused by the porcine GGTA1 gene would occur within minutes to hours after xenotransplantation, thereby leading to death of the animals or humans transplanted with the organ. Since this is very fatal to organ transplantation, the present inventors have made efforts to solve this problem; the present inventors tried to prepare pigs in which the HO-1 and sTNFR1-Fc genes are simultaneously expressed while the GGTA1 gene is completely knocked out.

Specifically, the sequence of the gene coding for GGTA1 can be obtained from a known gene database, and can be included in the scope of the present invention without limitation as long as it is a gene corresponding to protein exhibiting the activity of GGTA1 in pigs.

As used herein, the term "gene knock-out" refers to an artificial manipulation aiming at the loss of function of genes, and may be caused by insertion, substitution, deletion, etc. of some nucleotides in genes or by deletion of all or part of genes from a genome.

The gene knock-out is not particularly limited as long as it is a known knock-out method, and it can be included within the scope of the present invention. For example, the gene knock-out may be carried out using transcription activator-like effector nuclease (TALEN).

As used herein, the term "TALEN" refers to a nuclease capable of recognizing and cleaving a target region of DNA, and specifically refers to a fusion protein comprising a TALE domain and a nucleotide cleavage domain. In the present invention, the terms "TAL effector nuclease" and "TALEN" can be used interchangeably. The TAL effector is known as a protein secreted by the Type III secretion system of *Xanthomonas* bacteria when a variety of plant species is infected by the *Xanthomonas* bacteria. The protein may bind to a promoter sequence in a host plant to activate the expression of a plant gene that aids in bacterial infection. The protein recognizes plant DNA sequences through a central repeating domain comprising a variable number of amino acid repeats up to 34. Therefore, TALE may be a new platform for tools in genome engineering. However, in order to prepare functional TALEN with genome-editing activity, a few key parameters that have not been known to date should be defined as follows: (i) the minimum DNA-binding domain of TALE, (ii) the length of the spacer between two half-spaces constituting one target region, and (iii) the linker connecting the FokI nuclease domain to dTALE or a fusion junction.

The TALE domain of the present invention refers to a protein that binds to a nucleotide in a nucleotide in a sequence-specific manner via one or more TALE-repeat modules. The TALE domain comprises at least one TALE-repeat module, more specifically 1 to 30 TALE-repeat modules, but is not limited thereto. In the present invention, the terms "TAL effector domain" and "TALE domain" are interchangeable. The TALE domain may comprise half of a TALE-repeat module. With respect to TALEN, the contents of the entire disclosure of International Patent Publication No. WO 2012/093833 or US Patent Publication No. 2013-0217131 are included in the present specification as a reference material.

In the present invention, the TALEN can be used to knock out the GGTA1 gene. In particular, the TALEN may target exon 9 of the GGTA1 gene, but is not limited thereto.

In a specific embodiment of the present invention, TALEN for knocking out the GGTA1 gene was prepared by targeting the exon 9 region, which plays a crucial role in the catalysis of the GGTA1 enzyme (FIG. 3). In another specific embodiment of the present invention, the prepared TALEN was transduced into fibroblasts simultaneously expressing the gene coding for human HO-1 and the gene coding for human sTNFR1-Fc fusion protein to prepare cells in which the gene coding for GGTA1 is knocked out (FIG. 4).

Figure 5:
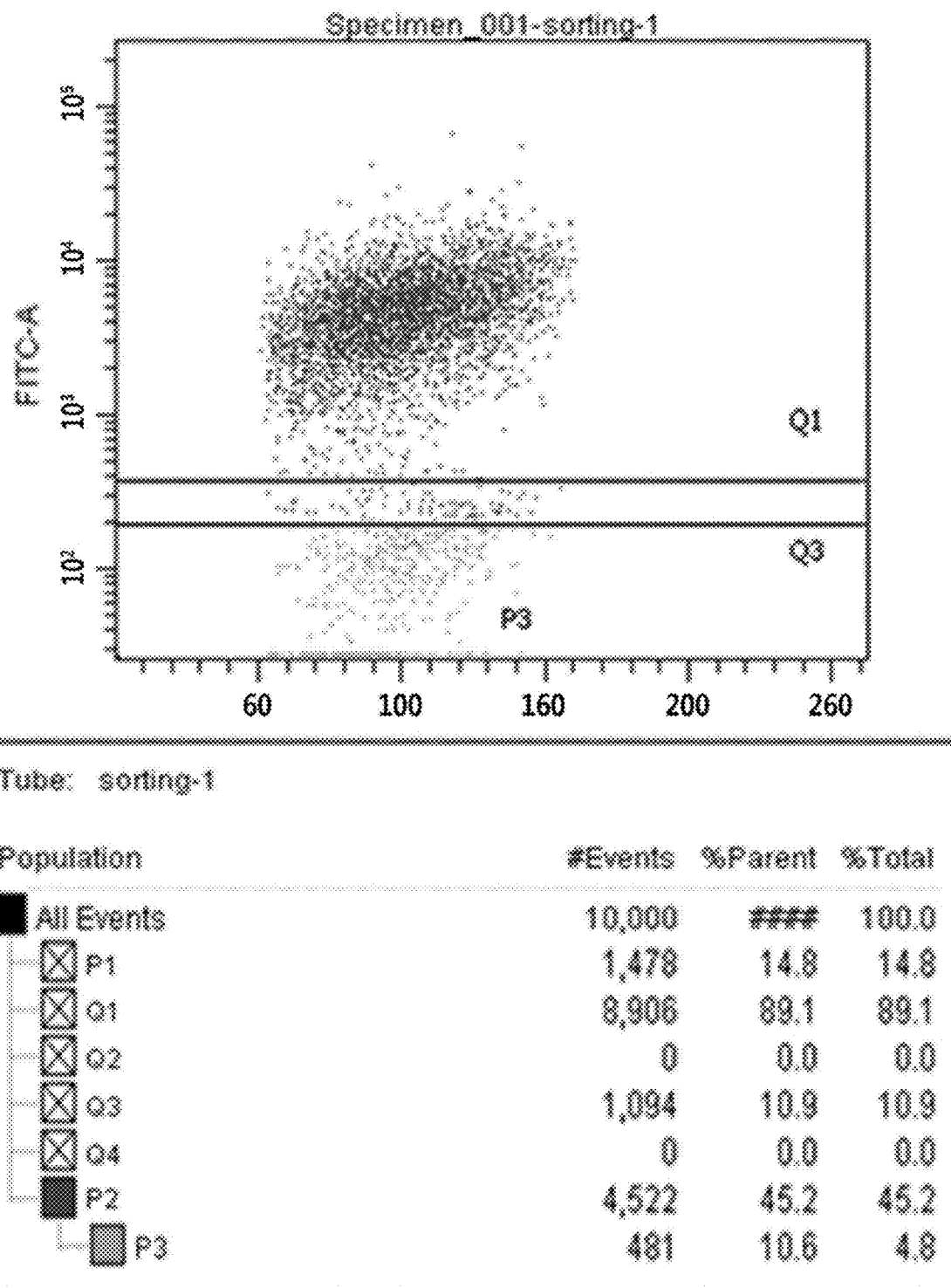
FIG. 5 shows the result of the magnetic-activated cell sorting method for TALEN-mediated mutant pig cells.

Thereafter, the cells were isolated using magnetic beads to obtain a cell population in which the GGTA1 gene was deleted (FIG. 5).

In step b), the introduction of a single vector including the gene coding for human HO-1 and a single vector including the gene coding for human TNFR1-Fc fusion protein and the knocking out of the gene coding for GGTA1 may be carried out simultaneously or separately. In addition, the order thereof is not particularly limited as long as the same genotype of the cells can be produced.

In step c), the somatic cells introduced with the expression vector of step b) can be easily selected by using the expression vector introduced with a selection marker. The selection marker may be an antibiotic resistance gene. Examples of the antibiotic resistance gene may include $bsd^r$, $neo^r$, $pac^r$, $bsr^r$, and $hph^r$, but are not limited thereto. In one specific embodiment of the present invention, the somatic cells introduced with the expression vector comprising the gene coding for human HO-1 were selected using $neo^r$ by treatment of the cell culture broth with neomycin, and the somatic cells introduced with the expression vector including the gene coding for human TNFR1-Fc fusion protein were selected using $bsd^r$ by treatment of the cell culture broth with blasticidin.

In another embodiment, selection of somatic cells in which the gene coding for GGTA1 is knocked out by using TALEN may be carried out using a TALEN plasmid including a reporter system, but is not limited thereto. The reporter system may use, for example, an $H2K^K$ membrane protein. In this case, the cells expressing the gene can be selected using magnetic beads. After colonies were formed from the selected cells, T7E1 analysis, targeted deep sequencing, etc. may be carried out for each of the colonies to additionally determine whether the gene coding for GGTA1 is knocked out.

Step d) is a step of producing an embryo having genetic traits which are identical to those of the somatic cells by using the selected somatic cells, and it is intended to produce a clone pig having the somatic cells. Specifically, step d) is a step of removing the nucleus from an oocyte of a pig and fusing it with the selected somatic cells to prepare an embryo transplanted with a somatic cell nucleus, and is a step of using a technology for somatic cell nuclear transfer.

In step d), the oocyte of the present invention may be used by culturing an immature oocyte collected from the ovary of gilts.

As used herein, the term "nuclear transfer" means transfer of the nucleus of a cell into an enucleated oocyte, and an individual born by implantation of the nucleus transferred embryos is a genetically identical animal clone because genetic material of the same donor cell is transferred into the recipient cytoplast.

To remove the genetic materials of the oocytes, various methods such as physical enucleation, chemical treatment, and centrifugation with cytochalasin B treatment are employed (Tatham et al., *Hum Reprod.*, 11(7); 1499-1503, 1996). In the present invention, the physical enucleation method using a micromanipulator was used. The transduced somatic cells are introduced into an enucleated oocyte by using the techniques such as a cell fusion method, intracytoplasmic microinjection, or the like. The cell fusion method is simple and useful for large-scale production of embryos. The intracytoplasmic microinjection permits maximum exposure of a nucleus to the cytosol in recipient cytoplasts. The fusion of a somatic cell and an enucleated oocyte is accomplished by changing viscosity on the cell surface by electric pulse. It is convenient to use an electro-cell manipulator so that the pulse length and voltage are easily controllable. In the specific embodiment of the present invention, physical enucleation was performed by micromanipulation, and fusion of the enucleated oocyte and the selected somatic donor cell line was performed by electric pulse to prepare embryos.

The method of the present invention for producing a transgenic pig may further include a step of implanting the embryo of step d) into a porcine uterus. For this purpose, the surrogate mother for implantation of the somatic cell nuclear transferred embryo is preferably an individual in estrus.

The nuclear-transferred embryos are activated and developed to the implantable stage, and then implanted in the surrogate mother. The activation of cloned embryo induces reinitiation of the cell cycle, which is temporarily quiescent, whereby the cleavage of embryo is possible. To activate a cloned embryo, the activation of cell cycle arrest factors, such as MPF, MAP kinase, or the like, should be suppressed, in which, for the suppression of the activation, the increase of intracellular calcium ions in a cloned embryo is necessary. The activation of cell cycle arrest factors can be directly suppressed by the dramatic increase of calcium influx induced by electro-stimulation or chemical treatment such as ionomycin, 6-DMAP, or the like, in which the above methods can be used independently or together.

In a specific embodiment of the present invention, it was confirmed by PCR (FIG. 6) and Western blotting (FIGS. 7 and 8) that the HO-1 and sTNFR1-Fc genes, which were inserted into all of the transgenic pigs produced by the method above, were expressed. In addition, it was confirmed through nucleotide sequence analysis (FIG. 9) and FACS analysis (FIG. 10) that the GGTA1 gene was knocked out.

Figure 11:
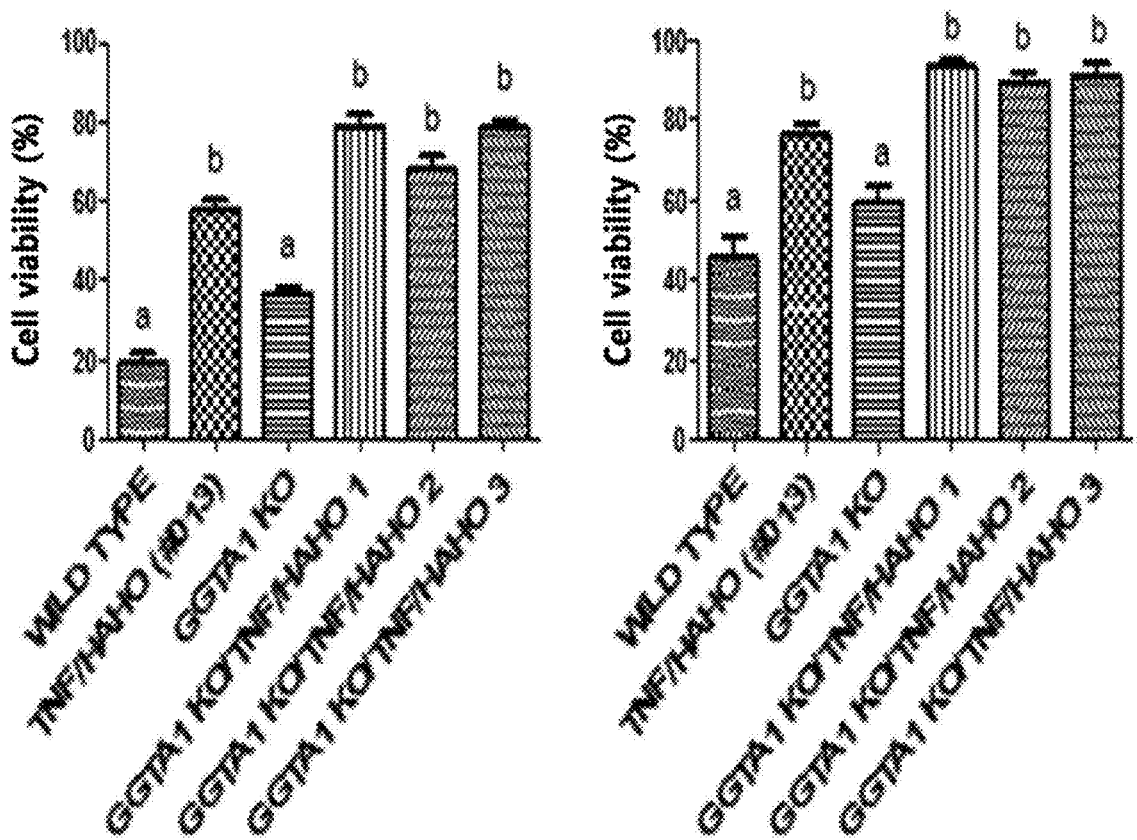
FIG. 11 shows graphs confirming cell viability in fibroblasts of transgenic pigs, which were treated with hTNF-α and CHX, i.e., apoptotic stimulations, for 15 minutes, and treated with $H_2O_2$, i.e., oxidative stress stimulation, for 1 hour; thereafter, CCK-8 was used to examine the result.
Figure 12:
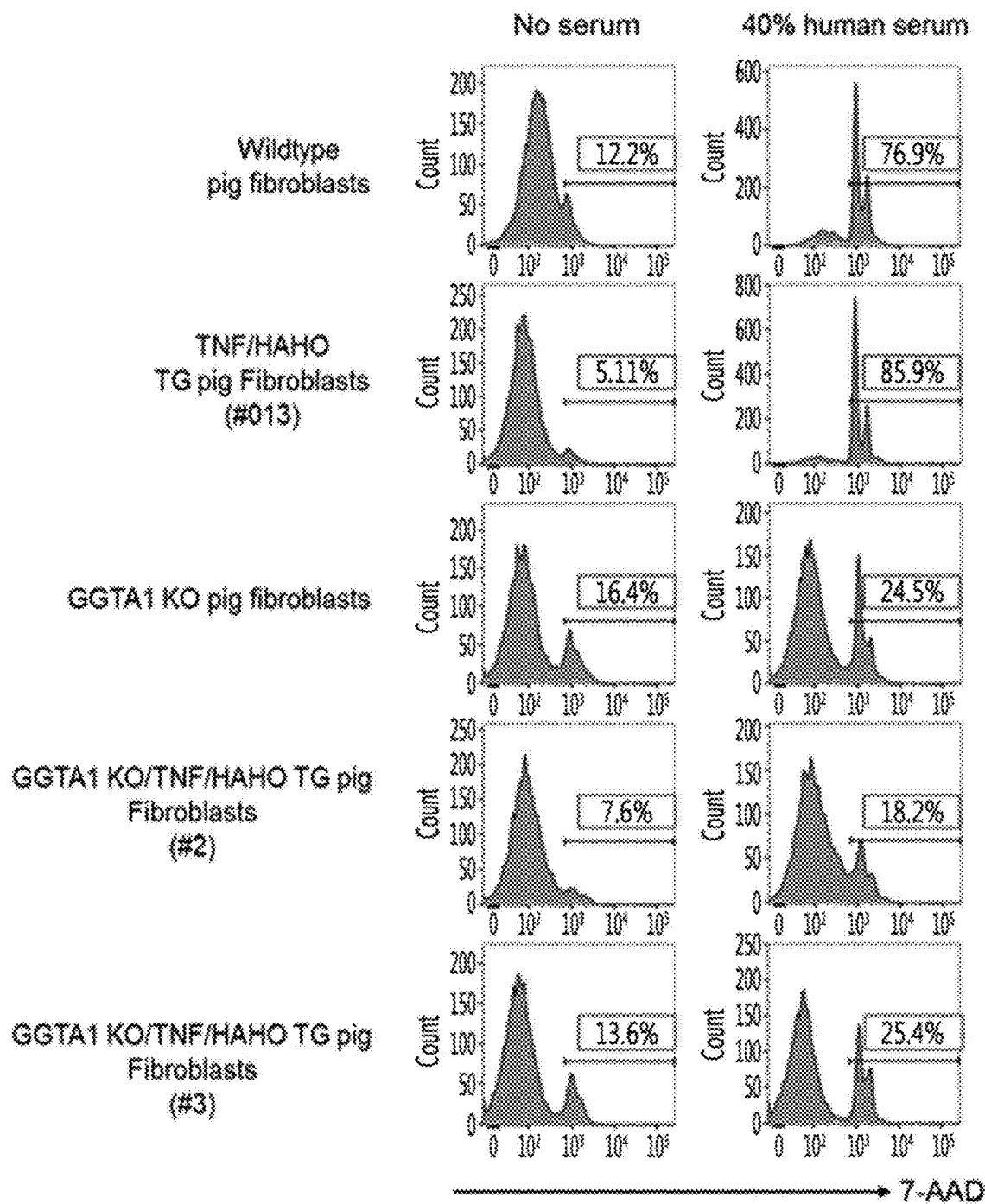
FIG. 12 shows the result of antibody-/complement-mediated lysis in fibroblasts of transgenic pigs by using a fluorescence-activated cell sorting method by 7-AAD staining after treating with 40% human serum.
Figure 13:
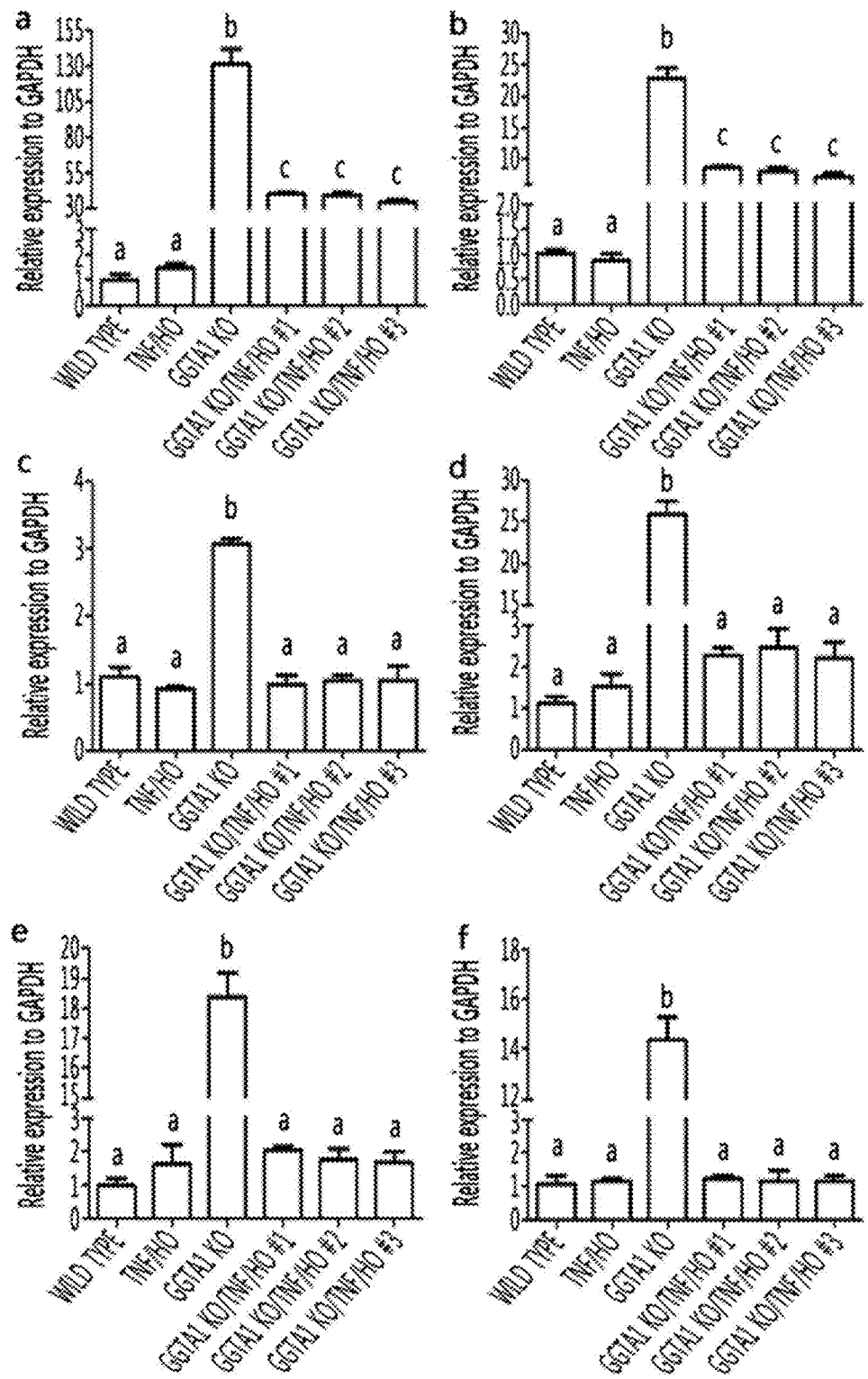
FIG. 13 shows the graphs confirming the expression of sialyltransferase (i.e., wild-type, shRNFR1-Fc-hHAHO-1, GGTA1 knock-out, and GGTA1 knock-out/shTNFR1-Fc-hHAHO-1) in skin fibroblasts derived from pigs ((a) ST3Gal2, (b) ST3Gal3, (c) ST3Gal4, (d) ST6GalNac1, (e) ST6GalNac2, and (f) ST6GalNac6).

In another specific embodiment of the present invention, the cell viability against apoptotic stimulation and oxidative stress stimulation was analyzed using the fibroblasts isolated from the transgenic pig. As a result, it was confirmed that the cell viability was significantly increased compared to wild-type fibroblasts (FIG. 11). Additionally, it was confirmed that the fibroblasts isolated from the transgenic pig were resistant to human serum and complement (FIG. 12), and that the expression level of non-Gal antigen was decreased in spite of GGTA1 knock-out (FIG. 13).

Accordingly, it was confirmed that when the method of the present invention for producing the transgenic pig was used, the transgenic pig, in which the gene coding for human HO-1 and the gene coding for TNFR1-Fc fusion protein were stably expressed and the gene coding for GGTA1 was knocked out, was able to be produced, and that the organs isolated from the pig were highly viable against oxidative stress, had resistance to human serum and complement, and decreased the expression level of non-Gal antigen. Therefore, it can be seen that during transplantation of the organ isolated from the transgenic pig, cells or tissues are protected from oxidative stress and an immune rejection response is inhibited.

Accordingly, the transgenic pig of the present invention has an additional feature of knocking out the GGTA1 gene in comparison with a conventional pig in which the genes coding for human HO-1 and TNFR1-Fc fusion protein are simultaneously expressed. In this regard, the transgenic pig of the present invention is resistant to human serum and complement due to the GGTA1 knock-out. Furthermore, it was confirmed that in the transgenic pig of the present invention, the expression level of non-Gal antigen, which may be a disadvantage of the GGTA1 knock-out, was low.

Therefore, the transgenic pig of the present invention may be very useful for xenotransplantation without an immune rejection response.

Another aspect of the present invention provides a transgenic pig for organ transplantation in which an immune rejection response is suppressed during xenotransplantation, wherein a gene coding for human HO-1 and a gene coding for human TNFR1-Fc fusion protein are introduced and a gene coding for GGTA1 is knocked out. Specifically, the organ may be a pancreatic islet, a pancreas, a heart, a kidney, a liver, a lung, and a cornea, but is not limited thereto. In addition, any pig's organs can be included without limitation as long as these can be transplanted into humans.

Still another aspect of the present invention provides a somatic donor cell line for producing the transgenic pig.

The somatic donor cell line stably expresses the gene coding for human HO-1 and the gene coding for human TNFR1-Fc protein. In addition, the cell line in which the gene coding for GGTA1 is knocked out can be used without limitation.

Still another aspect of the present invention provides a method for producing a transplantable organ in which an immune rejection response is suppressed during xenotransplantation, comprising: producing a transgenic pig by the method for producing the transgenic pig; and isolating a transplantable organ from the transgenic pig. Specifically, the organ may be a pancreatic islet, a pancreas, a heart, a kidney, a liver, a lung, a cornea, etc., but is not limited thereto. In addition, any pig's organs can be included without limitation as long as these can be transplanted into humans. Further, since an immune rejection response does not occur when the organ is transplanted into humans, it is possible to treat diseases according to the type of a desired organ.

DETAILED DESCRIPTION

Hereinbelow, the present invention will be described in detail with accompanying exemplary embodiments. However, the exemplary embodiments disclosed herein are only for illustrative purposes and should not be construed as limiting the scope of the present invention.

Example 1: Construction of the Gene Coding for HO-1 and the Gene Coding for sTNFR1-Fc Protein-Expressing Vectors The gene coding for HO-1 and the gene coding for sTNFR1-Fc protein were each cloned to prepare expression vectors. Thereafter, these were introduced into cells to produce a cell line simultaneously expressing the genes. The cloning and transduction were carried out in the same manner as described in Korean Patent Publication No. 10-2011-0079485, specifically as follows.

1-1. Construction of the Gene Coding for HO-1-Expressing Vector and Test on Gene Expression The sequence of the gene coding for human HO-1 was analyzed using the NCBI website (ncbi.nlm.nih.gov) and ExPASy website (expasy.org), and was used to prepare its forward (SEQ ID NO: 2) and reverse primers (SEQ ID NO: 3). Polymerase chain reaction (PCR) was performed using the primer set to obtain the gene coding for HO-1 (SEQ ID NO: 1). For expression of the gene, a pcDNA3.1 vector (Invitrogen, CA, USA), which is an expression vector comprising a neomycin resistance gene, was treated with NheI and EcoRI restriction enzymes, and the obtained gene coding for HO-1 was inserted into the restriction sites so as to construct a gene coding for HO-1-expressing vector (FIG. 1).

In order to examine expression of the inserted gene, an HEK293 cell line was transfected with the gene coding for HO-1-expressing vector using Lipofectamine™2000 (Invitrogen, CA, USA). The HEK293 cell line was seeded in a 35 mm plastic culture dish (Becton Dickinson, NJ, USA) at a cell density of $3\times10^5$, and the next morning, 1 μg of HO-1-expressing vector was diluted with 50 μL of Opti-MEM I Reduced Serum Medium (Invitrogen, CA, USA), and Lipofectamine™2000 in an equal volume to the HO-1-expressing vector was also diluted with 50 μL of Opti-MEM I, and incubated at room temperature for 5 minutes. After incubation, the diluted HO-1-expressing vector and the diluted Lipofectamine™2000 were mixed with each other, and incubated at room temperature for 20 minutes. After incubation, the mixture was added to the cells in the 35 mm cell culture dish, and cultured at 37° C. in a $CO_2$ incubator. After 4 hours, the media was replaced with DMEM (Invitrogen, CA, USA) supplemented with 10% FBS and penicillin/streptomycin, and cultured at 37° C. in a $CO_2$ incubator.

After 48 hours, cells were harvested using a lysis buffer (lysis buffer: 1% Triton X-100, 50 mM TrisHCl, 20 mM NaF, 150 mM NaCl, protease inhibitors), and 30 μg of cell lysate was electrophoresed and then transferred onto a PVDF membrane. The PVDF membrane was blocked with a blocking buffer (5% skim milk in TBST) for 1 hour, and reacted with anti HO-1 antibody (rabbit monoclonal antibody, Abcam, Cambridge, UK) diluted at 1:2000 at room temperature for 1 hour. After reaction, the membrane was washed with TBST buffer for 30 minutes three times, and reacted with HRP-conjugated anti-rabbit IgG antibody (Santa Cruz Biotechnology, CA, USA) diluted at 1:5000 at room temperature for 1 hour. After reaction, the membrane was washed with TBST buffer for 30 minutes three times, and treated with chemiluminescent substrates (WestSaveUp™, Abfrontier, Seoul, Korea), followed by exposure on X-ray film and development. As a result, it was confirmed that the gene coding for human HO-1 was inserted into the vector and expressed.

1-2. Construction of the Gene Coding for sTNFR1-Fc Fusion Protein-Expressing Vector and Test on Gene Expression The sequence of the gene coding for human TNFR1 protein was analyzed using the NCBI website (ncbi.nlm.nih.gov) and ExPASy website (expasy.org), and was used to prepare forward (SEQ ID NO: 4) and reverse primers (SEQ ID NO: 5) of the extracellular domain of tumor necrosis factor receptor 1. In addition, the sequence of human immunoglobulin G1 gene was analyzed to prepare forward (SEQ ID NO: 6) and reverse primers (SEQ ID NO: 7) of an Fc region. PCR was performed using each primer set to obtain soluble TNFR1 and IgG1-Fc fusion gene (sTNFR1-Fc, SEQ ID NO: 8). For expression of the gene, a pcDNA6 vector (Invitrogen, CA, USA), which is an expression vector including a blasticidin resistance gene, was treated with HindIII and XhoI restriction enzymes, and the obtained gene coding for sTNFR1 and IgG1-Fc fusion protein was inserted into the restriction sites so as to construct a gene coding for sTNFR1-Fc protein-expressing vector (FIG. 2).

In order to examine expression of the inserted gene, an HEK293 cell line was transfected with the gene coding for sTNFR1-Fc protein-expressing vector using Lipofectamine™2000 (Invitrogen, CA, USA). The HEK293 cell line was seeded in a 35 mm plastic culture dish (Becton Dickinson, NJ, USA) at a cell density of $3 \times 10^5$, and the next morning, 1 µg of the gene coding for sTNFR1-Fc protein-expressing vector was diluted with 50 µL of Opti-MEM I Reduced Serum Medium (Invitrogen, CA, USA), and Lipofectamine™2000 in an equal volume to the sTNFR1-Fc-expressing vector was also diluted with 50 µL of Opti-MEM I, and incubated at room temperature for 5 minutes. After incubation, the diluted sTNFR1-Fc-expressing vector and the diluted Lipofectamine™2000 were mixed with each other, and incubated at room temperature for 20 minutes. After incubation, the mixture was added to the cells in the 35 mm cell culture dish, and cultured at 37° C. in a $CO_2$ incubator. After 4 hours, the media was replaced with serum-free DMEM (Invitrogen, CA, USA) supplemented with penicillin/streptomycin, and cultured at 37° C. in a $CO_2$ incubator.

After 48 hours, the culture broth and cell lysate were subjected to Western blotting using anti-hIgG antibody (Santa Cruz Biotechnology, CA, USA). The cell lysate and culture broth was electrophoresed, and then transferred onto a PVDF membrane. The PVDF membrane was blocked with a blocking buffer (5% skim milk in TBST) for 1 hour, and then reacted with HRP-conjugated anti-human IgG antibody (Santa Cruz Biotechnology, CA, USA) diluted at 1:5000 at room temperature for 1 hour. After reaction, the membrane was washed with TBST buffer three times, and treated with chemiluminescent substrates (WestSaveUp™, Abfrontier, Seoul, Korea), followed by exposure on X-ray film and development. As a result, protein expression of soluble TNFR1-Fc was confirmed.

Example 2: Treatment of Transcription Activator-Like Effector Nuclease (TALEN) for the Production of Cells GGTA1 Knock-Out Cells and Colony Recovery TALEN for knocking out the gene coding for GGTA1 was prepared (FIG. 3).

The target region of TALEN is exon 9, which plays a crucial role in the catalytic site of the GGTA1 enzyme. TALEN, which can recognize and bind to a specific sequence of the gene, was prepared and inserted into a plasmid. The cell line transduced by TALEN was found and recovered by using a reporter system in which a target gene sequence of TALEN and reporter genes such as GFP and $H2K^K$ are inserted.

Specifically, fibroblasts were isolated from a newborn pig of the transgenic pig shTNFRI-Fc-F2A-HA-HO-1 (TNF/HAHO, #013), which had been previously produced (Korean Patent Publication No. 10-2011-0079485). The resultants were then cultured using a DMEM medium (Invitrogen, Carlsbad, Calif., USA) supplemented with 10% FBS. The TALEN plasmid and reporter system for GGTA1 was transduced into the fibroblasts using Lipofectamine™2000 (Invitrogen, Carlsbad, Calif., USA). After 48 hours, the cells were incubated with IB4-FITC (isolectin B4-conjugated fluorescein isothiocyanate, Sigma) for 30 minutes, and then washed with PBS. IB4-negative cells were isolated using FACS. The cell number was increased via cell culture and used for genomic DNA isolation and somatic cell nuclear transfer.

PCR was carried out with a swine α-gal-specific primer using the isolated DNA. The PCR product was inserted into a pGEM T-easy vector (Promega Inc.) to analyze the nucleotide removal efficiency by TALEN in the chromosome. As an alternative method, the reporter plasmid and the TALEN plasmid containing the gene of $H2K^K$ membrane expression protein were transduced for 48 hours, and then cells were selected by a MACS separation system using MACSelect $H2K^K$ microBeads (Miltenyi Biotec.). The selected cells were subjected to negative separation using IB4-biotin and streptavidin-conjugated microbeads. The separated cells were cultured in a 100 mm dish at a low density (200 cells/dish) to form each colony. Each colony was transferred to a 48-well plate to increase the number of cells, and mutations were screened by T7E1 analysis.

For the T7E1 analysis, the site of the gene coding for GGTA1, i.e., a target site, was amplified by PCR. The amplified sequence was denatured by heating, and T7 endonuclease I was synthesized by treating at 37° C. for 20 minutes to form a heterogeneous complex, which was confirmed on a 2% agarose gel. Two positive cell colonies were integrated and used as donor cells for somatic cell nuclear transfer. The T7E1 analysis was once more performed on the transgenic pigs produced from the cells, and the knock-out was confirmed.

Example 3: FACS Analysis

Attempts were made to verify the cell line using a FACS. First, the cultured fibroblasts were trypsinized and washed with PBS, followed by incubation with the IB4-FITC on ice for 30 minutes in order to analyze the expression of Gal-α-1,3-Gal epitope. The cells were then washed and suspended in PBS and analyzed with the CELLQUEST software (Becton Dickinson) using FACS Caliber (Becton-Dickinson, CA).

Example 4: Somatic Cell Nuclear Transfer

After removing all of the cumulus cells from oocytes matured in vitro, the nuclei and pole nuclei of the oocytes were stained with 5 µg/mL of hoechst 33342. The stained oocytes were fixed with a holding micropipette, and enucleation was performed using a suction pipette in a TALP medium supplemented with 5 µg/mL cytochalasin B. The enucleated oocytes were placed in the TALP medium and continuously used for somatic cell nuclear transfer. One of the transgenic somatic cells, which had been knocked out, was injected into the peritoneal cavity of the enucleated oocytes and then allowed to precipitate for 4 minutes in a fusion medium containing 0.26 M mannitol, 0.1 mM $MgSO_4$, and 0.5 mM HEPES. Thereafter, electrical stimulation was applied using the BTX Electro-Cell Manipulator at a DC voltage of 1.2 kV/cm once for 30 µs duration to induce cytoplasmic fusion between the cytoplasms of the enucleated oocytes and the injected somatic cells. After 20 to 30 minutes of the fusion, electrical stimulation was applied to the reconstituted embryos in an active medium supplemented with 0.26 M mannitol, 0.5 mM HEPES, 0.1 mM $CaCl_2$), and 0.1 mM $MgSO_4$ using the BTX Electro-Cell Manipulator at a DC voltage of 1.5 kV/cm and once for 60 µs duration, and thereby the reconstituted embryos were activated. The activated clone embryos were incubated in PZM-5 (porcine zygote medium-5; IFP0410P, Funakoshi, Tokyo, Japan), which is an incubator maintained with 5% carbon dioxide, 5% oxygen, and 90% nitrogen for 1 to 2 days. Morphologically normal embryos (one-cell stage at day 1; two- to eight-cell stages at day 2) were selected for embryo transfer. Thereafter, 90 to 120 embryos were transplanted to the synchronized surrogate mother through a laparotomy. The protocol for using animals was approved by the Institutional Animal Care and Use Committee in Seoul National University in accordance with their guidelines for the management and use of experimental animals (SNU-141120-8).

Example 5: Evaluation of Cell Viability of Fibroblasts of the Transgenic Pigs

Fibroblasts ($1\times10^5$ cells/well) isolated from each of a wild-type pig, a GGTA1 knocked out pig, a TNF/HAHO transgenic pig, and three GGTA1 KO/TNF/HAHO transgenic pigs were plated on a 24-well plate, treated with TNF-α (20 ng/mL) and CHX (cycloheximide, 10 μg/mL) for 15 hours, and then treated with $H_2O_2$ for 1 hour. Cell viability thereof was measured using a CCK-8 solution according to the manufacturer's manual (Dojindo Laboratories, Kumamoto, Japan). In this evaluation, fibroblasts derived from wild-type Yucatan pigs were used as a control group. Absorbance was measured with a microplate reader (Tecan Sunrise, Hayward, Calif., USA).

Example 6: Western Blot Analysis

Tail-derived fibroblasts and various organs were separated and dissolved in a PRO-PREP protein extraction solution (iNtRON Biotechnology, Inc.), diluted in an SDS buffer (GeneDepot), and then incubated at 100° C. for 5 minutes. Equal amounts of proteins were loaded onto 10% SDS-PAGE. Proteins were electrophoresed and transferred to a polyvinylidene difluoride (PVDF) membrane. After electrophoresis, the PVDF membrane was blocked with 5% skim milk, reacted with HRP-conjugated anti-human IgG antibody (1:2000, Binding Site, Birmingham, UK), anti-hHO-1 antibody (Abcam, MA, USA), or anti-HA antibody (Abcam, MA, USA) diluted at 1:4000, and then incubated at 4° C. for 24 hours. The blots were developed using a Pierce SuperSignal West Pico Chemiluminescent System (Thermo Fisher Scientific).

Example 7: Evaluation of Complement-Mediated Lysis of Porcine Fibroblasts

In order to evaluate natural antibodies against α-Gal antigens, complement-mediated cytotoxicity was measured. Fibroblasts ($1\times10^5$ cells) derived from the wild-type pig, GGTA1 knock-out pig, shTNFRI-Fc-F2A-HA-hHO-1 transgenic pig, and shTNFRI-Fc-F2A-HA-hHO-1/GGTA1 knock-out transgenic pig were removed and transferred to a 1.5 mL tube. The resultants were treated with human serum (Sigma Aldrich, MO, USA) and incubated at room temperature for 1 hour. Cell viability was measured using 7-AAD (BD Bioscience, CA, USA) in FACS Canto (BD Bioscience, CA, USA).

Test Example 1: Establishment of GGTA1 Gene Knock-Out Cell Line

The GGTA1 gene was knocked out using TALEN targeting GGTA1, and the deletion of the GGTA1 gene which had been selected using the MACS method was confirmed. In addition, the qualitative analysis thereof was confirmed by cloning and sequencing (FIG. 4). As a result, it was confirmed that some nucleotides were deleted at the target position of the GGTA1 gene in the selected cells, and that the GGTA1 gene was knocked out.

The method of selecting cells in which the GGTA1 gene is knocked out is a method using magnetic beads; that is, it is a method of culturing the antibody conjugated with magnetic beads for $H2K^K$ with cells and then isolating the cells using the column (FIG. 5). A population of cells in which the GGTA1 gene is knocked out was obtained by the method above.

Test Example 2: Verification of Gene Insertion in Transgenic Clone Pigs

Figure 6:
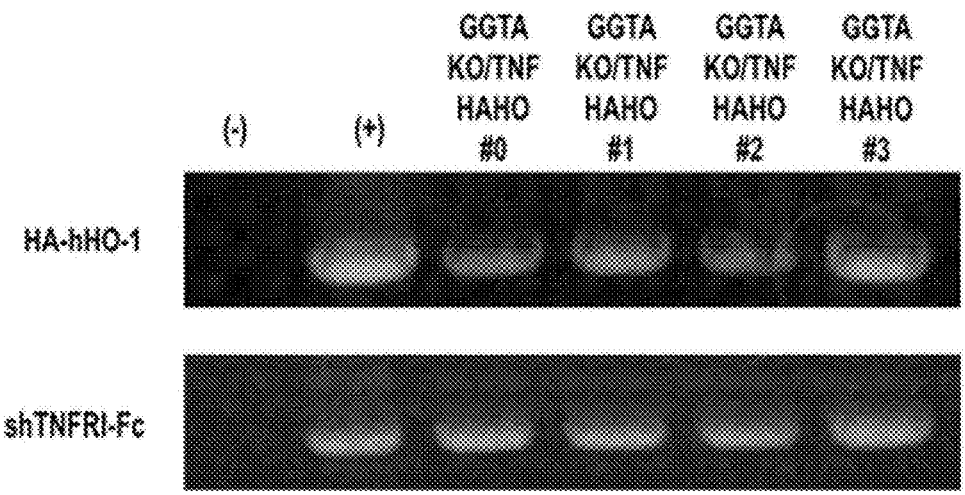
FIG. 6 shows the result of PCR to examine expression of the gene coding for HO-1 and the gene coding for sTNFR1-Fc protein in transgenic pigs.
Figure 7:
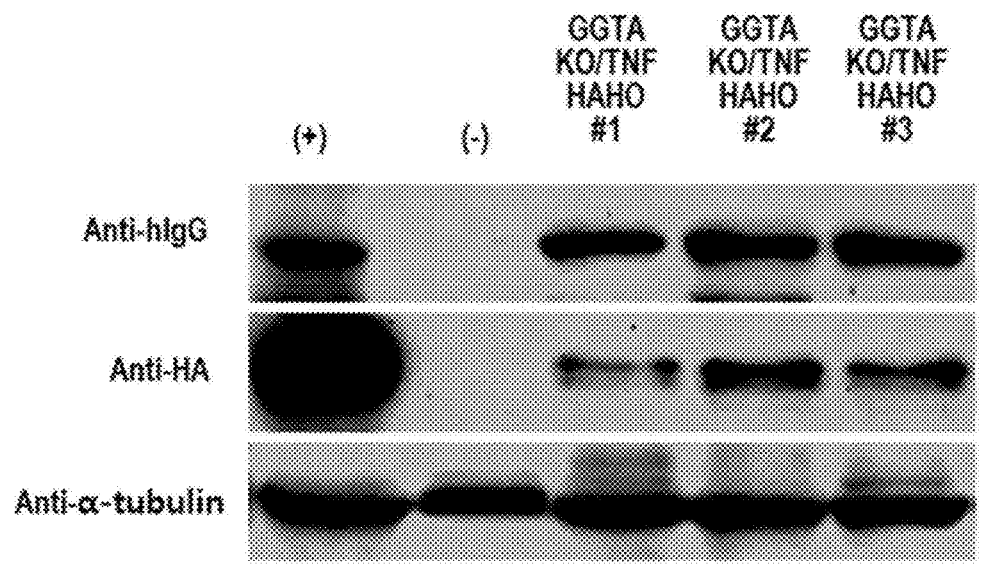
FIG. 7 shows the result of Western blot analysis to examine protein expression of the HO-1 and sTNFR1-Fc proteins in transgenic pigs.

DNA was extracted from oocyte and donor cells of the transgenic pigs, and PCR was carried out using primers specific for each gene. As a result, it was confirmed that the HO-1 and sTNFR1-Fc genes were inserted in all of the produced transgenic pigs (FIG. 6). The Western blot was carried out for the HO-1 and sTNFR1-Fc proteins in the transgenic pig-derived fibroblasts (FIG. 7) and organs (FIG. 8), and as a result, it was confirmed that the size of bands corresponding to the protein type of each gene was clearly observed.

Figures 8, 9:
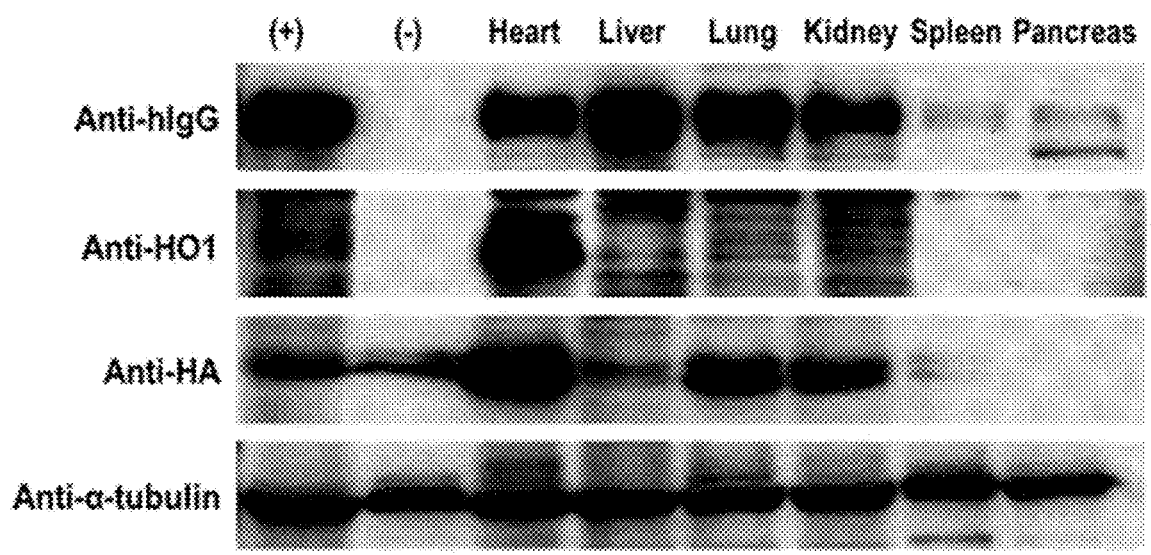
FIG. 8 shows the result of Western blot analysis to examine the protein expression of the HO-1 and sTNFR1-Fc proteins in organs of transgenic pigs.
FIG. 9 shows the result of the TALEN-mediated GGTA1 gene mutation, which was produced by somatic cell cloning, on a nucleotide sequence.
Figure 10:
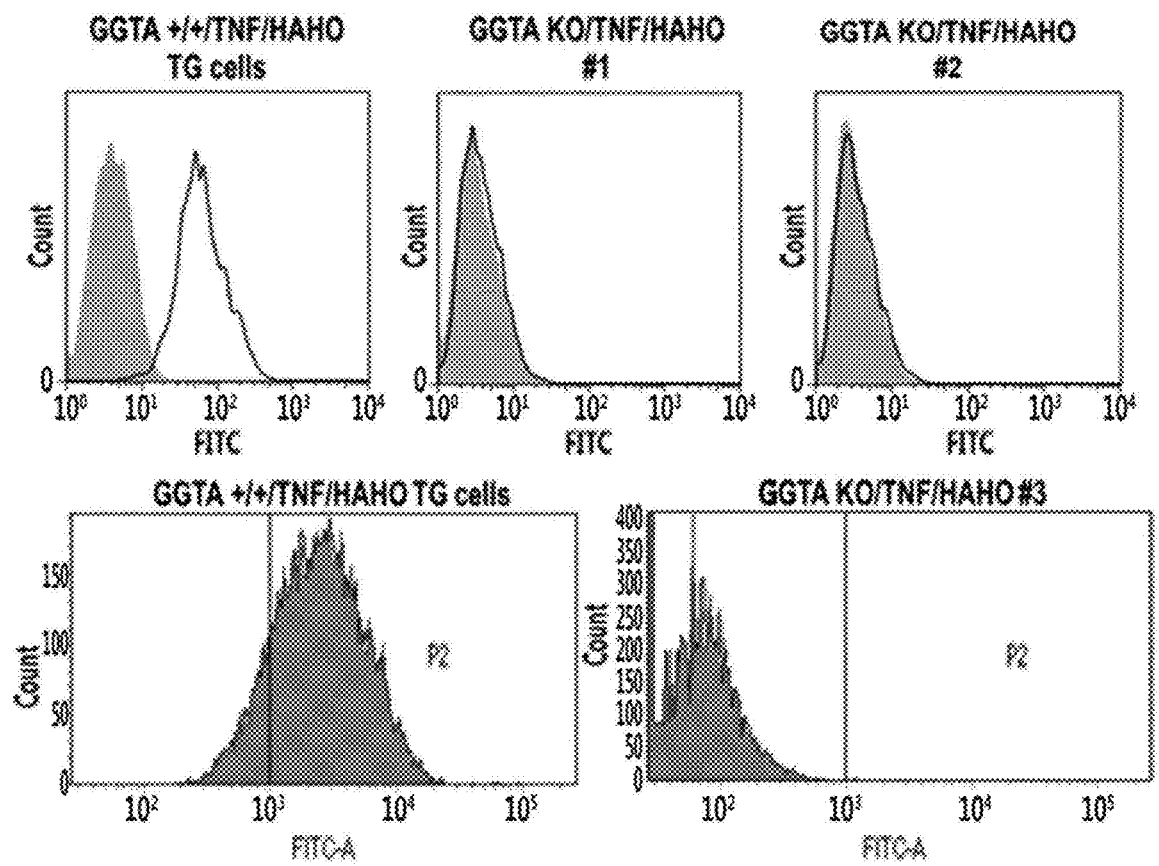
FIG. 10 shows the result of examination of the deletion of α-1,3-Gal epitopes by using flow cytometry in fibroblasts derived from transgenic pigs' tails.

Test Example 3: Verification of Deletion of the GGTA1 Gene in Transgenic Clone Pigs The transgenic clone pigs were tested for genetic variation. DNA was extracted from each pig which had been produced, and the nucleotide sequence at the exon 9 position of the GGTA1 gene, which corresponds to the target of TALEN, was analyzed. As a result of the analysis, it was confirmed that each of 18-, 6-, and 29-nucleotide sequences of the GGTA1 gene was deleted in each transgenic clone pig (FIG. 9). Due to the deletion of each nucleotide sequence, the amino acid sequence was also deleted in the order of 6, 2, 9, etc., and thus the loss of functions of the GGTA1 gene was also expected. The results of the FACS analysis using antibodies showed that the GGTA1 gene was deleted (FIG. 10). This suggests that it is possible to overcome the hyper-acute rejection response when xenotransplantation of the organs derived from the transgenic clone pigs is applied.

Test Example 4: Validation of Function Through Cell Viability Analysis

Cell viability against apoptotic stimulation (TNFα and CHX) and oxidative stress stimulation ($H_2O_2$) was examined by CCK-8 assay using each pig-derived fibroblast. As a result, it was confirmed that in the fibroblasts derived from the three GGTA1 KO/shTNFRI-Fc-HA-hHO-1 transgenic clone pigs, cell viability was significantly increased compared to wild-type fibroblasts (FIG. 11). This suggests that the viability of the transplanted cells will be increased upon xenotransplantation the organs derived from the transgenic clone pigs.

Test Example 5: Validation of Function Through Antibody/Complement-Mediated Lytic Reaction of the Gene Deletion 7-AAD staining was carried out using the fibroblasts derived from each pig, from which antibody/complement-mediated lysis by human serum was examined. As a result, it was confirmed that the fibroblasts derived from the GGTA1 KO/shTNFRI-Fc-HA-hHO-1 transgenic pigs were more resistant to the human serum and complement compared to those derived from the shTNFRI-Fc-HA-hHO-1 transgenic pigs (FIG. 12). This suggests that the antibody/complement-mediated lytic reaction will be reduced when xenotransplantation of the organs derived from the transgenic clone pigs is applied.

Test Example 6: Identification of Expression of Sialyl Gene

The sialyl gene is one of the representative non-Gal antigens, and overexpression of the non-Gal antigen may be a problem when the single gene coding for GGTA1 is knocked out. Therefore, the expression level of the non-Gal antigen was examined in the cells derived from the wild-type pigs, the transgenic pigs in which the HO-1 and TNFR1-Fc are simultaneously expressed while the GGTA1 gene is knocked out, the transgenic pigs in which the HO-1 and TNFR1-Fc genes are simultaneously expressed, and the transgenic pigs in which the single GGTA1 gene is knocked out (FIG. 13).

As a result, it was confirmed that the expression level of ST3Gal2 and ST3Gal3 in the three pigs in which the HO-1 and TNFR1-Fc gene are simultaneously expressed while the GGTA1 gene is knocked out was higher than that in the wild-type pigs and the transgenic pigs in which HO-1 and TNFR1-Fc genes are simultaneously expressed, but was lower than that in the transgenic pigs in which the single GGTA1 gene is knocked out. Additionally, it was confirmed that for ST3Gal4, ST6GalNac1, ST6GalNac2, and ST6GalNac6, the expression level thereof in the transgenic pigs in which HO-1 and TNFR1-Fc genes are simultaneously expressed while the GGTA1 gene is knocked out was similar to that in the wild-type pigs and the transgenic pigs in which the HO-1 and TNFR1-Fc genes are simultaneously expressed.

These results suggest that the expression of the non-Gal antigen may be increased by the deletion of only GGTA1 gene, and thus the problem of an immune rejection response may be caused during xenotransplantation; however, by simultaneously expressing the HO-1 and TNFR1-Fc genes, the expression level of the non-Gal antigen was reduced. That is, in the transgenic pig of the present invention, the antibody/complement-mediated lytic reaction was significantly reduced compared to the transgenic pig in which the gene HO-1 and TNFR1-Fc genes are simultaneously expressed, and thus the hyper-acute immune response is inhibited during xenotransplantation. Therefore, the expression of the non-Gal antigen in the transgenic pig of the present invention was reduced compared to that in the transgenic pig in which the GGTA1 gene is knocked out.

Accordingly, the transgenic pig of the present invention may produce organs in which the immune rejection response is suppressed during xenotransplantation, and thus can be effectively used for the organ transplantation.

From the foregoing, one of ordinary skill in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A method of producing a pig nuclear transfer embryo comprising: (a) obtaining a somatic cell from a pig; (b) introducing a transgene encoding a heme oxygenase-1 (HO-1) and a transgene encoding a tumor necrosis factor 1-Fc (TNFR1-Fc) into the somatic cell, wherein the transgenes incorporate into the genome of the somatic cell, and introducing a homozygous disruption into endogenous genes encoding α-1,3-galactosyltransferase (GGTA1) in the somatic cell, thereby producing a genetically modified pig somatic cell comprising in its genome a transgene encoding HO-1, a transgene encoding a TNFR1-Fc, and a homozygous disruption of the endogenous GGTA1 genes; and (c) introducing the genetically modified pig somatic cell into an enucleated pig oocyte to produce a pig nuclear transfer embryo.

2. The method according to claim 1, wherein the transgene encoding the HO-1 comprises the nucleic acid sequence of SEQ ID NO: 1.

3. The method according to claim 1, wherein the transgene encoding the TNFR1-Fc comprises the nucleic acid sequence of SEQ ID NO: 8.

4. The method according to claim 1, wherein in step b), a single vector comprising the transgene coding for HO-1 and a single vector comprising the transgene coding for TNFR1-Fc are introduced separately or simultaneously into the somatic cell.

5. The method according to claim 1, wherein introducing the homozygous disruption into the endogenous genes comprises introducing a TALEN that specifically binds and cleaves a nucleic acid sequence in the endogenous genes.

6. The method according to claim 5, wherein the TALEN specifically binds to and causes a double stranded break in exon 9 of the endogenous GGTA1 gene.

7. The method according to claim 1, further comprising:
 d) transferring the pig nuclear transfer embryo into a recipient female pig; and
 e) allowing the recipient female pig to gestate until offspring are produced.

8. A transgenic pig comprising in its genome (i) an exogenous nucleic acid encoding a human heme oxygenase-1 (HO-1) gene; (ii) an exogenous nucleic acid encoding a human tumor necrosis factor receptor 1 fusion protein (TNFR1-Fc); and (iii) a homozygous disruption of the endogenous gene encoding alpha-1,3, galactosyltransferase (GGTA1), wherein the transgenic pig simultaneously expresses the HO-1 and TNFR1-Fc and lacks expression of the GGTA1, and wherein (i) cells of the transgenic pig have greater resistance to apoptotic and oxidative stress stimulation compared to wild type cells; (ii) cells are more resistant to the human serum and complement compared to those derived from a transgenic pigs comprising in its genome exogenous nucleic acids encoding HO-1 and TNFR1-Fc but the endogenous GGTA1 is intact; and (iii) the antibody/complement-mediated lytic reaction is significantly reduced compared to the transgenic pigs comprising in its genome exogenous nucleic acids encoding HO-1 and TNFR1-Fc but the endogenous GGTA1 is intact.

9. A somatic cell line derived from the transgenic pig of claim 8.

10. A method for producing a transplantable organ in which an immune rejection response is suppressed during xenotransplantation, comprising:
 producing a transgenic pig by the method of claim 7; and
 isolating a transplantable organ from the transgenic pig.

11. The method according to claim 10, wherein the organ is at least one selected form the group consisting of a pancreas, a heart, a kidney, a liver, a lung, and a cornea.

* * * * *

SEQUENCE LISTING

<160> NUMBER OF SEQ ID NOS: 32

<210> SEQ ID NO 1
<211> LENGTH: 867
<212> TYPE: DNA
<213> ORGANISM: Artificial Sequence
<220> FEATURE:
<223> OTHER INFORMATION: HO-1

<400> SEQUENCE: 1

```
atggagcgtc cgcaacccga cagcatgccc caggatttgt cagaggccct gaaggaggcc        60
accaaggagg tgcacaccca ggcagagaat gctgagttca tgaggaactt tcagaagggc       120
caggtgaccc gagacggctt caagctggtg atggcctccc tgtaccacat ctatgtggcc       180
ctggaggagg agattgagcg caacaaggag agcccagtct tcgccctgt ctacttccca        240 gaagagctgc accgcaaggc tgccctggag caggacctgg ccttctggta cgggccccgc       300
tggcaggagg tcatcccta cacaccagcc atgcagcgct atgtgaagcg gctccacgag       360
gtggggcgca cagagcccga gctgctggtg gcccacgcct acacccgcta cctgggtgac       420
ctgtctgggg gccaggtgct caaaaagatt gcccagaaag ccctggacct gcccagctct       480
ggcgagggcc tggccttctt caccttcccc aacattgcca gtgccaccaa gttcaagcag       540
ctctaccgct cccgcatgaa ctccctggag atgactcccg cagtcaggca gagggtgata       600
gaagaggcca agactgcgtt cctgctcaac atccagctct tgaggagtt gcaggagctg        660 ctgacccatg acaccaagga ccagagcccc tcacgggcac cagggcttcg ccagcgggcc       720
```

```
agcaacaaag tgcaagattc tgcccccgtg gagactccca gagggaagcc cccactcaac        780
acccgctccc aggctccgct tctccgatgg gtccttacac tcagctttct ggtggcgaca        840
gttgctgtag ggctttatgc catgtga                                           867
```

```
<210> SEQ ID NO 2
<211> LENGTH: 33
<212> TYPE: DNA
<213> ORGANISM: Artificial Sequence
<220> FEATURE:
<223> OTHER INFORMATION: Forward primer for HO-1

<400> SEQUENCE: 2
cgggctagca ccatggagcg tccgcaaccc gac                                    33

<210> SEQ ID NO 3
<211> LENGTH: 30
<212> TYPE: DNA
<213> ORGANISM: Artificial Sequence
<220> FEATURE:
<223> OTHER INFORMATION: Reverse primer for HO-1

<400> SEQUENCE: 3
cgggaattct cacatggcat aaagccctac                                        30

<210> SEQ ID NO 4
<211> LENGTH: 27
<212> TYPE: DNA
<213> ORGANISM: Artificial Sequence
<220> FEATURE:
<223> OTHER INFORMATION: Forward primer for sTNFR1

<400> SEQUENCE: 4
ataagcttat gggcctctcc accgtgc                                           27

<210> SEQ ID NO 5
<211> LENGTH: 22
<212> TYPE: DNA
<213> ORGANISM: Artificial Sequence
<220> FEATURE:
<223> OTHER INFORMATION: Reverse primer for sTNFR1

<400> SEQUENCE: 5
tgtggtgcct gagtcctcag tg                                                22

<210> SEQ ID NO 6
<211> LENGTH: 23
<212> TYPE: DNA
<213> ORGANISM: Artificial Sequence
<220> FEATURE:
<223> OTHER INFORMATION: Forward primer for human IgG-Fc

<400> SEQUENCE: 6
acatgcccac cgtgcccagc acc                                               23

<210> SEQ ID NO 7
<211> LENGTH: 28
<212> TYPE: DNA
<213> ORGANISM: Artificial Sequence
<220> FEATURE:
<223> OTHER INFORMATION: Reverse primer for human IgG-Fc

<400> SEQUENCE: 7
atctcgagtc atttacccgg agacaggg                                          28
```

```
<210> SEQ ID NO 8
<211> LENGTH: 1305
<212> TYPE: DNA
<213> ORGANISM: Artificial Sequence
<220> FEATURE:
<223> OTHER INFORMATION: Human sTNFR1-Fc

<400> SEQUENCE: 8
atgggcctct ccaccgtgcc tgacctgctg ctgccactgg tgctcctgga gctgttggtg      60
ggaatatacc cctcaggggt tattggactg gtccctcacc taggggacag ggagaagaga     120
gatagtgtgt gtccccaagg aaaatatatc caccctcaaa ataattcgat ttgctgtacc     180
aagtgccaca aaggaaccta cttgtacaat gactgtccag gccgggggca ggatacggac     240
tgcagggagt gtgagagcgg ctccttcacc gcttcagaaa accacctcag acactgcctc     300
agctgctcca atgccgaaaa ggaaatgggt caggtggaga tctcttcttg cacagtggac     360
cgggacaccg tgtgtggctg caggaagaac cagtaccggc attattggag tgaaaacctt     420
ttccagtgct tcaattgcag cctctgcctc aatgggaccg tgcacctctc tgccaggag      480
aaacagaaca ccgtgtgcac ctgccatgca ggtttctttc taagagaaaa cgagtgtgtc     540
tcctgtagta actgtaagaa aagcctggag tgcacgaagt tgtgcctacc ccagattgag     600
aatgttaagg gcactgagga ctcaggcacc acaacatgcc caccgtgccc agcacctgaa     660
ctcctggggg gaccgtcagt cttcctcttc cccccaaaac ccaaggacac cctcatgatc     720
tcccggaccc ctgaggtcac atgcgtggtg gtggacgtga gccacgaaga ccctgaggtc     780
aagttcaact ggtacgtgga cggcgtggag gtgcataatg ccaagacaaa gccgcgggag     840
gagcagtaca acagcacgta ccgtgtggtc agcgtcctca ccgtcctgca ccaggactgg     900
ctgaatggca aggagtacaa gtgcaaggtc tccaacaaag ccctcccagc ccccatcgag     960
aaaaccatct ccaaagccaa agggcagccc cgagaaccac aggtgtacac cctgccccca    1020
tcccgggatg agctgaccaa gaaccaggtc agcctgacct gcctggtcaa aggcttctat    1080
cccagcgaca tcgccgtgga gtgggagagc aatgggcagc cggagaacaa ctacaagacc    1140
acgcctcccg tgctggactc cgacggcccc ttcttcctct acagcaagct caccgtggac    1200
aagagcaggt ggcagcaggg gaacgtcttc tcatgctccg tgatgcatga ggctctgcac    1260
aaccactaca cgcagaagag cctctccctg tctccgggta aatga                    1305

<210> SEQ ID NO 9
<211> LENGTH: 18
<212> TYPE: DNA
<213> ORGANISM: Artificial Sequence
<220> FEATURE:
<223> OTHER INFORMATION: Reverse primer for HO-1

<400> SEQUENCE: 9
aaggtgaaga aggccagg                                                    18

<210> SEQ ID NO 10
<211> LENGTH: 52
<212> TYPE: DNA
<213> ORGANISM: Artificial Sequence
<220> FEATURE:
<223> OTHER INFORMATION: GGTA1 sequence targeted by TALEN

<400> SEQUENCE: 10
tccagcacga ggtggacttc ctcttctgca tggacgtgga tcaggtcttc ca              52

<210> SEQ ID NO 11
```

```
<211> LENGTH: 71
<212> TYPE: DNA
<213> ORGANISM: Artificial Sequence
<220> FEATURE:
<223> OTHER INFORMATION: wild type GGTA1 sequence

<400> SEQUENCE: 11
cccacatcca gcacgaggtg gacttcctct tctgcatgga cgtggatcag gtcttccaaa      60
acaactttgg g                                                          71

<210> SEQ ID NO 12
<211> LENGTH: 63
<212> TYPE: DNA
<213> ORGANISM: Artificial Sequence
<220> FEATURE:
<223> OTHER INFORMATION: TALEN disrupted GGTA1 sequence No. 3

<400> SEQUENCE: 12
cccacatcca gcacgaggtg gacgtccatg gacgtggatc aggtcttcca aaacaacttt      60
ggg                                                                   63

<210> SEQ ID NO 13
<211> LENGTH: 68
<212> TYPE: DNA
<213> ORGANISM: Artificial Sequence
<220> FEATURE:
<223> OTHER INFORMATION: TALEN disrupted GGTA1 sequence No. 6

<400> SEQUENCE: 13
cccacatcca gcacgaggtg gacttcctct gcatggacgt ggatcaggtc ttccaaaaca      60
actttggg                                                              68

<210> SEQ ID NO 14
<211> LENGTH: 67
<212> TYPE: DNA
<213> ORGANISM: Artificial Sequence
<220> FEATURE:
<223> OTHER INFORMATION: TALEN disrupted GGTA1 sequence No. 1

<400> SEQUENCE: 14
cccacatcca gcacgaggtg gacttctctg catggacgtg gatcaggtct tccaaaacaa      60
ctttggg                                                               67

<210> SEQ ID NO 15
<211> LENGTH: 72
<212> TYPE: DNA
<213> ORGANISM: Artificial Sequence
<220> FEATURE:
<223> OTHER INFORMATION: TALEN disrupted GGTA1 sequence No. 2

<400> SEQUENCE: 15
cccacatcca gcacgaggtg gacttcctct tctggcatgg acgtggatca ggtcttccaa      60
aacaactttg gg                                                         72

<210> SEQ ID NO 16
<211> LENGTH: 66
<212> TYPE: DNA
<213> ORGANISM: Artificial Sequence
<220> FEATURE:
<223> OTHER INFORMATION: TALEN disrupted GGTA1 sequence No. 5

<400> SEQUENCE: 16
cccacatcca gcacgaggtg gtgctcatcc atggacgtgg atcaggtctt ccaaaacaac      60
``` tttggg                                                             66

<210> SEQ ID NO 17
<211> LENGTH: 58
<212> TYPE: DNA
<213> ORGANISM: Artificial Sequence
<220> FEATURE:
<223> OTHER INFORMATION: TALEN disrupted GGTA1 sequence No. 9

<400> SEQUENCE: 17
cccacatcca gcacgaggtg gacctgacgt ggatcaggtc ttccaaaaca actttggg    58

<210> SEQ ID NO 18
<211> LENGTH: 53
<212> TYPE: DNA
<213> ORGANISM: Artificial Sequence
<220> FEATURE:
<223> OTHER INFORMATION: TALEN disrupted GGTA1 sequence No. 4

<400> SEQUENCE: 18
cccacatcca gcacgaggtg gacgtggatc aggtcttcca aaacaacttt ggg         53

<210> SEQ ID NO 19
<211> LENGTH: 47
<212> TYPE: DNA
<213> ORGANISM: Artificial Sequence
<220> FEATURE:
<223> OTHER INFORMATION: TALEN disrupted GGTA1 sequence No. 8

<400> SEQUENCE: 19
cccacatcca gcacgaggtg gatcaggtct tccaaaacaa ctttggg                47

<210> SEQ ID NO 20
<211> LENGTH: 47
<212> TYPE: DNA
<213> ORGANISM: Artificial Sequence
<220> FEATURE:
<223> OTHER INFORMATION: TALEN disrupted GGTA1 sequence No. 10

<400> SEQUENCE: 20
cccacatcca gcacgaggta gatcaggtct tccaaaacaa ctttggg                47

<210> SEQ ID NO 21
<211> LENGTH: 70
<212> TYPE: DNA
<213> ORGANISM: Artificial Sequence
<220> FEATURE:
<223> OTHER INFORMATION: TALEN disrupted GGTA1 sequence No. 7

<400> SEQUENCE: 21
cccacatcca gcacgaggtg gacttcctct ctgcatggac gtggatcagg tcttccaaaa  60
caactttggg                                                        70

<210> SEQ ID NO 22
<211> LENGTH: 68
<212> TYPE: DNA
<213> ORGANISM: Artificial Sequence
<220> FEATURE:
<223> OTHER INFORMATION: consensus GGTA1 sequence forTALEN disruption

<400> SEQUENCE: 22
cccacatcca gcacgaggtg gacttcctct gcatggacgt ggatcaggtc ttccaaaaca  60
actttggg                                                          68

```
<210> SEQ ID NO 23
<211> LENGTH: 130
<212> TYPE: DNA
<213> ORGANISM: Artificial Sequence
<220> FEATURE:
<223> OTHER INFORMATION: A wild type GGTA1 sequence

<400> SEQUENCE: 23
gaggtggcaa gacatcagca tgatgcgcat gaagaccatc ggggagcaca tcctggccca      60
catccagcac gaggtggact tcctcttctg catggacgtg gatcaggtct tccaaaacaa     120
ctttggggtg                                                            130

<210> SEQ ID NO 24
<211> LENGTH: 113
<212> TYPE: DNA
<213> ORGANISM: Artificial Sequence
<220> FEATURE:
<223> OTHER INFORMATION: TALEN disrupted GGTA1 sequence from Piglet #1

<400> SEQUENCE: 24
gaggtggcaa gacatcagca tgatgcgcat gaagaccatc ggggagcaca tcctggccca      60
catccagcac gaggtggacc gtggatcagg tcttccaaaa caactttggg gtg            113

<210> SEQ ID NO 25
<211> LENGTH: 129
<212> TYPE: DNA
<213> ORGANISM: Artificial Sequence
<220> FEATURE:
<223> OTHER INFORMATION: A wild type GGTA1 sequence

<400> SEQUENCE: 25
gatgcgcatg aagaccatcg gggagcacat cctggcccac atccagcacg aggtggactt      60
cctcttctgc atggacgtgg atcaggtctt ccaaaacaac tttggggtgg agaccctggg     120
ccagtcggt                                                             129

<210> SEQ ID NO 26
<211> LENGTH: 112
<212> TYPE: DNA
<213> ORGANISM: Artificial Sequence
<220> FEATURE:
<223> OTHER INFORMATION: TALEN disrupted GGTA1 sequence from Piglet #2

<400> SEQUENCE: 26
gatgcgcatg aagaccatcg gggagcacat cctggcccac atccagcacg aggtggacgt      60
ggatcaggtc ttccaaaaca actttggggt ggagaccctg gccagtcgg tg              112

<210> SEQ ID NO 27
<211> LENGTH: 130
<212> TYPE: DNA
<213> ORGANISM: Artificial Sequence
<220> FEATURE:
<223> OTHER INFORMATION: A wild type GGTA1 sequence

<400> SEQUENCE: 27
caagacatca gcatgatgcg catgaagacc atcggggagc acatcctggc ccacatccag      60
cacgaggtgg acttcctctt ctgcatggac gtggatcagg tcttccaaaa caactttggg     120
gtggagaccc                                                            130

<210> SEQ ID NO 28
<211> LENGTH: 124
```

```
<212> TYPE: DNA
<213> ORGANISM: Artificial Sequence
<220> FEATURE:
<223> OTHER INFORMATION: TALEN disrupted GGTA1 sequence from Piglet #2

<400> SEQUENCE: 28
caagacatca gcatgatgcg catgaagacc atcggggagc acatcctggc ccacatccag    60
cacgaggtgg acttcctcat ggacgtggat caggtcttcc aaaacaactt tggggtggag   120
accc                                                                124

<210> SEQ ID NO 29
<211> LENGTH: 130
<212> TYPE: DNA
<213> ORGANISM: Artificial Sequence
<220> FEATURE:
<223> OTHER INFORMATION: A wild type GGTA1 sequence

<400> SEQUENCE: 29
ccatcgggga gcacatcctg gcccacatcc agcacgaggt ggacttcctc ttctgcatgg    60
acgtggatca ggtcttccaa aacaactttg gggtggagac cctgggccag tcggtggctc   120
agctacaggc                                                          130

<210> SEQ ID NO 30
<211> LENGTH: 100
<212> TYPE: DNA
<213> ORGANISM: Artificial Sequence
<220> FEATURE:
<223> OTHER INFORMATION: TALEN disrupted GGTA1 sequence from Piglet #3

<400> SEQUENCE: 30
ccatcgggga gcacatcctg gcccacatcc agcacgaggt ggacttccaa aacaactttg    60
gggtggagac cctgggccag tcggtggctc agctacaggc                         100

<210> SEQ ID NO 31
<211> LENGTH: 130
<212> TYPE: DNA
<213> ORGANISM: Artificial Sequence
<220> FEATURE:
<223> OTHER INFORMATION: A wild type GGTA1 sequence

<400> SEQUENCE: 31
tcagcatgat gcgcatgaag accatcgggg agcacatcct ggcccacatc cagcacgagg    60
tggacttcct cttctgcatg gacgtggatc aggtcttcca aaacaacttt ggggtggaga   120
ccctgggcca                                                          130

<210> SEQ ID NO 32
<211> LENGTH: 100
<212> TYPE: DNA
<213> ORGANISM: Artificial Sequence
<220> FEATURE:
<223> OTHER INFORMATION: TALEN disrupted GGTA1 sequence from Piglet #3

<400> SEQUENCE: 32
tcagcatgat gcgcatgaag accatcgggg agcacatcct ggcccacatc cagcacgagg    60
tggacttcca aaacaacttt ggggtggaga ccctgggcca                         100
```